US010869916B2

(12) United States Patent
Ichim et al.

(10) Patent No.: US 10,869,916 B2
(45) Date of Patent: *Dec. 22, 2020

(54) THERAPEUTIC IMMUNE MODULATION BY STEM CELL SECRETED EXOSOMES

(71) Applicant: XON Cells, Inc., Germantown, MD (US)

(72) Inventors: Thomas Ichim, San Diego, CA (US); Vladimir Bogin, San Diego, CA (US)

(73) Assignee: XON Cells, Inc., Germantown, MD (US)

( * ) Notice: Subject to any disclaimer, the term of this patent is extended or adjusted under 35 U.S.C. 154(b) by 25 days.

This patent is subject to a terminal disclaimer.

(21) Appl. No.: 16/016,234

(22) Filed: Jun. 22, 2018

(65) Prior Publication Data

US 2018/0369351 A1 Dec. 27, 2018

Related U.S. Application Data

(63) Continuation of application No. 15/228,036, filed on Aug. 4, 2016, now abandoned, which is a continuation of application No. 13/756,310, filed on Jan. 31, 2013, now Pat. No. 9,427,450.

(60) Provisional application No. 61/592,636, filed on Jan. 31, 2012.

(51) Int. Cl.
| | | |
|---|---|---|
| *A61K 35/28* | (2015.01) | |
| *A61K 35/12* | (2015.01) | |
| *A61K 39/008* | (2006.01) | |
| *A61K 39/00* | (2006.01) | |
| *A61K 48/00* | (2006.01) | |

(52) U.S. Cl.
CPC .......... *A61K 39/0008* (2013.01); *A61K 35/12* (2013.01); *A61K 35/28* (2013.01); *A61K 48/00* (2013.01)

(58) Field of Classification Search
None
See application file for complete search history.

(56) References Cited

U.S. PATENT DOCUMENTS

| | | |
|---|---|---|
| 6,448,287 B1 | 9/2002 | Casciari et al. |
| 7,015,037 B1 | 3/2006 | Furcht et al. |
| 7,399,632 B2 | 7/2008 | Simmons et al. |
| 2004/0071770 A1 | 4/2004 | Smith |
| 2005/0271697 A1 | 12/2005 | Litvack |
| 2006/0292164 A1 | 12/2006 | Horwitz |
| 2007/0122393 A1 | 5/2007 | McIntosh et al. |
| 2007/0160588 A1 | 7/2007 | Kihm |
| 2008/0063652 A1 | 3/2008 | Pykett et al. |
| 2008/0159998 A1 | 7/2008 | Ichim |
| 2008/0241113 A1 | 10/2008 | Walton et al. |
| 2008/0260704 A1 | 10/2008 | Riordan et al. |
| 2009/0053182 A1 | 2/2009 | Ichim et al. |
| 2012/0107413 A1 | 5/2012 | Lim et al. |
| 2013/0156726 A1 | 6/2013 | Ichim et al. |
| 2014/0065240 A1 | 3/2014 | Mitsialis et al. |
| 2017/0247708 A1 | 8/2017 | Katakowski et al. |

FOREIGN PATENT DOCUMENTS

| | | |
|---|---|---|
| EP | 1876233 A1 | 1/2008 |
| WO | WO-2006/078034 A1 | 7/2006 |

OTHER PUBLICATIONS

Abeyta et al., "Unique Gene Expression Signatures of Independently-Derived Human Embryonic Stem Cell Lines", Human Molecular Genetics, 13(6), pp. 601-608 (2004).
Abusamra et al., "Tumor Exosomes Expressing Fas Ligand Mediate CD8+ T-Cell Apoptosis", Blood Cells, Molecules & Diseases, vol. 35, pp. 169-173 (2005).
Airas et al., "Immunoregulatory Factors in Multiple Sclerosis Patients During and After Pregnancy: relevance of natural killer cells", Clinical and Experimental Immunology, vol. 151, pp. 235-243 (2008).
Allegrucci et al., "Differences Between Human Embryonic Stem Cell Lines", Human Reproduction Update, 13(2), pp. 103-120 (2007).
Almqvist et al., "Serum-Derived Exosomes from Antigen-Fed Mice Prevent Allergic Sensitization in a Model of Allergic Asthma", Immunology, vol. 125, pp. 21-27 (2008).
Alonso et al., "Diacylglycerol Kinase Alpha Regulates the Formation and Polarisation of Mature Multivesicular Bodies Involved in the Secretion of Fas Ligand-Containing Exosomes in T Lymphocytes", Cell Death and Differentiation, vol. 18, pp. 1161-1173 (2011).
Alvarez-Erviti et al., "Delivery of siRNA to the Mouse Brain by Systemic Injection of Targeted Exosomes", Nature biotechnology, 29(4), pp. 341-345 (2011).
Alvarez-Erviti et al., "Lysosomal Dysfunction Increases Exosome-Mediated Alpha-Synuclein Release and Transmission", Neurobiology of Disease, vol. 42, pp. 360-367 (2011).
Arnold et al., "Effect of Normal Endometrial Stroma on Growth and Differentiation in Ishikawa Endometrial Adenocarcinoma Cells", Cancer Research, vol. 62, pp. 79-88 (2002).
Battke et al., "Tumour Exosomes Inhibit Binding of Tumour-Reactive Antibodies to Tumour Cells and Reduce ADCC", Cancer Immunology and Immunotherapy, vol. 60, pp. 639-648 (2011).
Benson et al., "Oral Administration of Myelin Basic Protein is Superior to Myelin in Suppressing Established Relapsing Experimental Autoimmune Encephalomyelitis", Journal of Immunology, 162(10), pp. 6247-6254 (1999).
Blum et al., "Advances in Cell-Based Therapy for Peripheral Vascular Disease", Atherosclerosis, vol. 223, pp. 269-277 (2012).

(Continued)

*Primary Examiner* — Michail A Belyavskyi
(74) *Attorney, Agent, or Firm* — Faegre Drinker Biddle & Reath LLP (57) ABSTRACT

Disclosed are methods, compositions of matter, and protocols useful for the induction of a therapeutic immune modulatory response through administration of exosomes derived from a stem cell source. In one embodiment, said stem cell source is endometrial regenerative cells. Specifically, in one embodiment stem cell derived exosomes are used as a method of treating an autoimmune condition such as rheumatoid arthritis, multiple sclerosis, or systemic lupus erythromatosis.

15 Claims, 2 Drawing Sheets

(56) References Cited

OTHER PUBLICATIONS

Buschow et al., "MHC Class II-Associated Proteins in B-Cell Exosomes and Potential Functional Implications for Exosome Biogenesis", Immunology and Cell Biology, vol. 88, pp. 851-856 (2010).
Capoccia et al., "Revascularization of Ischemic Limbs After Transplantation of Human Bone Marrow Cells with High Aldehyde Dehydrogenase Activity", Blood, 113(21), pp. 5340-5351 (May 2009).
Cervello et al., "Identification, Characterization and Co-Localization of Label-Retaining Cell Population in Mouse Endometrium With Typical Undifferentiated Markers", Human Reproduction, 22(1), pp. 45-51 (2007).
Chan et al., "Clonogenicity of Human Endometrial Epithelial and Stromal Cells", Biology of Reproduction, vol. 70, pp. 1738-1750 (2004).
Charoenviriyakul et al., "Cell type-specific and common characteristics of exosomes derived from mouse cell lines: Yield, physicochemical properties, and pharmacokinetics," European Journal of Pharmaceutical Sciences, vol. 96, 2017, pp. 316-322.
Clayton et al., "Cancer Exosomes Express CD39 and CD73, Which Suppress T Cells Through Adenosine Production", Journal of Immunology, vol. 187, pp. 676-683 (2011).
Cui et al., "Menstrual Blood-Derived Cells Confer Human Dystrophin Expression in the Murine Model of Duchenne Muscular Dystrophy via Cell Fusion and Myogenic Transdifferentiation", Molecular Biology of the Cell, vol. 18, pp. 1586-1594 (2007).
Da Silva Meirelles et al., "Mesenchymal Stem Cells Reside in Virtually all Post-Natal Organs and Tissues", Journal of Cell Science, vol. 119, pp. 2204-2213 (2006).
Durdu et al., "Autologous Bone-Marrow Mononuclear Cell Implantation for Patients with Rutherford Grade II-III Thromboangiitis Obliterans", J. Vasc. Surg., vol. 44, pp. 732-739 (2006).
Emmerich, "Stem Cells and Cardiovascular Therapy: results in peripheral artery disease", Bull Acad Natl Med., 193(3), pp. 549-557 (Mar. 2009)—Abstract Only.
Ernerudh et al., "Regulatory T Helper Cells in Pregnancy and Their Roles in Systemic Versus Local Immune Tolerance", American Journal of Reproductive Immunology, 65-Suppl1, pp. 31-43 (2011).
Faure et al., "Exosomes are Released by Cultured Cortical Neurons", Molecular and Cellular Neurosciences, vol. 31, pp. 642-648 (2006).
Fitzner et al., "Selective Transfer of Exosomes From Oligodendrocytes to Microglia by Macropinocytosis", Journal of Cell Science, vol. 124, pp. 447-458 (2011).
Forger et al., "Pregnancy Induces Numerical and Functional Changes of CD4+CD25 High Regulatory T Cells in Patients with Rheumatoid Arthritis", Annals of the Rheumatic Diseases, vol. 67, pp. 984-990 (2008).
Frangsmyr et al., "Cytoplasmic Microvesicular Form of Fas Ligand in Human Early Placenta: Switching the Tissue Immune Privilege Hypothesis From Cellular to Vesicular Level", Molecular Human Reproduction, 11 (1), pp. 35-41 (2004).
Gargett et al., "Endometrial Stem/Progenitor Cells and Proliferative Disorders of the Endometrium", Minerva Ginecologica, vol. 58, No. 6, pp. 511-526 (2006).
Gatson et al., "Induction of Pregnancy During Established EAE Halts Progression of CNS Autoimmune Injury via Pregnancy-Specific Serum Factors", Journal of Neuroimmunology, 230(1-2), pp. 105-113 (2011).
Greten et al., "Myeloid Derived Suppressor Cells in Human Diseases", International Immunopharmacology, 11(7), pp. 802-807 (2011).
Hafler et al., "Oral administration of Myelin Induces Antigen-specific TGF-β1 secreting T cells in Patients with Multiple Sclerosis", Annals of the New York Academy of Sciences, 835, pp. 120-131 (1997).
Hedlund et al., "Human Placenta Expresses and Secretes NKG2D Ligands via Exosomes that Down-Modulate the Cognate Receptor Expression: evidence for immunosuppressive function", Journal of Immunology, vol. 183, pp. 340-351 (2009).
Hida et al., "Novel Cardiac Precursor-Like Cells from Human Menstrual Blood-Derived Mesenchymal Cells", Stem Cells, vol. 26, pp. 1695-1704 (2008).
Higashi et al., "Oxidative Stress, Endothelial Function and Angiogenesis Induced by Cell Therapy and Gene Therapy", Current Pharmaceutical Biotechnology, 7(2), pp. 109-116 (2006) Abstract.
Hsu et al ., :Exosomes as a tumor vaccine: enhancing potency through direct loading of antigenic peptides, J. Immunol., vol. 26, No. 5, pp. 440-450 (2003).
Hwang et al., "Receptor-Mediated T Cell Absorption of Antigen Presenting Cell-Derived Molecules", Frontiers in Bioscience : a Journal and Virtual Library, vol. 16, pp. 411-421 (2011).
Ichim et al., "Feasibility of Combination Allogeneic Stem Cell Therapy for Spinal Cord Injury: a case report", International Archives of Medicine, 3(30), pp. 1-10 (2010).
Ichim et al., "Placental Mesenchymal and Cord Blood Stem Cell Therapy for Dilated Cardiomyopathy", Reproductive BioMedicine Online, 16(6), pp. 898-905 (2008).
Ichim et al., "Prevention of Allograft Rejection by in Vitro Generated Tolerogenic Dendritic Cells", Transplant Immunology, vol. 11, pp. 295-306 (2003).
Inamdar et al., "Emerging applications of exosomes in cancer therapeutics and diagnostics," Bioengineering & Translational Medicine 2017, vol. 2, pp. 70-80.
Iwase et al., "Comparison of Angiogenic Potency Between Mesenchymal Stem Cells and Mononuclear Cells in a Rat Model of Hindlimb Ischemia", Cardiovascular Research, vol. 66, pp. 543-551 (2005).
Janeway et al., "Immunobiology, 5th edition—The Immune System in Health and Disease", Immunobiology, Figure A.41—Immunity can be transferred by antibodies or by lymphocytes (2001).
Kara et al., "Fetal Cells Traffic to Injured Maternal Myocardium and Undergo Cardiac Differentiation", Circulation Research, 110(1), pp. 82-93 (2012).
Kebriaei et al., "Treatment of Graft-Versus-Host-Disease With Mesenchymal Stromal Cells", Cytotherapy, vol. 13, pp. 262-268 (2011).
Khashan et al., "Pregnancy and the Risk of Autoimmune Disease", PloS one, 6(5), pp. 1-7—e19658 (2011).
Kim et al., "MHC Class II+ Exosomes in Plasma Suppress Inflammation in an Antigen-Specific and Fas Ligand/Fas-Dependent Manner", Journal of Immunology, vol. 179, pp. 2235-2241 (2007).
Lachenal et al., "Release of Exosomes From Differentiated Neurons and its Regulation by Synaptic Glutamatergic Activity", Molecular and Cellular Neurosciences, 46(2), pp. 409-418 (2011).
Lai et al., "Mesenchymal Stem Cell Exosome: a novel stem cell-based therapy for cardiovascular disease", Regenerative Medicine, 6(4), pp. 481-492 (2011).
Lin et al., "Pathogenesis, Diagnosis, and Treatment of Recurrent Spontaneous Abortion with Immune Type", Frontiers of Medicine in China, 4(3), pp. 275-279 (2010).
Ludwig et al., "Exosomes: Small vesicles participating in intercellular communication", The International Journal of Biochemistry & Cell Biology, (2012).
Luketic et al., "Antigen Presentation by Exosomes Released From Peptide-Pulsed Dendritic Cells is not Suppressed by the Presence of Active CTL", Journal of Immunology, vol. 179, pp. 5024-5032, (2007).
March et al., "Cellular Approaches to Tissue Repair in Cardiovascular Disease: the more we know, the more there is to learn", Am. J. Physiol. Heart Circ. Physiol., vol. 287, pp. H458-H463, (2004).
Marleau et al., "Chimerism of Murine Fetal Bone Marrow by Maternal Cells Occurs in Late Gestation and Persists into Adulthood", Laboratory Investigation, 83(5), pp. 673-681 (2003).
Mathews et al., "CD23 Sheddase A Disintegrin and Metalloproteinase 10 (ADAM10) is also required for CD23 sorting into B cell-derived exosomes", The Journal of biological chemistry, 285(48), pp. 37531-37541 (2010).

(56) References Cited

OTHER PUBLICATIONS

Meng et al., "Endometrial Regenerative Cells: a novel stem cell population", Journal of Translational Medicine, vol. 5, pp. 57-68 (2007).
Mignot et al., "Prospects for exosomes in immunotherapy of cancer", J. Cell Mol. Med. vol. 10, No. 2, pp. 376-388 (2006).
Mincheva-Nilsson et al., "Placenta-Derived Soluble MHC Class I Chain-Related Molecules Down-Regulate NKG2D Receptor on Peripheral Blood Mononuclear Cells During Human Pregnancy: a possible novel immune escape mechanism for fetal survival", Journal of Immunology, vol. 176, pp. 3585-3592 (2006).
Mincheva-Nilsson et al., "The Role of Placental Exosomes in Reproduction", American Journal of Reproductive Immunology, vol. 63, pp. 520-533 (2010).
Murphy et al., "Allogeneic Endometrial Regenerative Cells: an 'Off the shelf solution' for critical limb ischemia", Journal of Translational Medicine, vol. 6, p. 45-53 (2008).
Oh, Sunok et al. (J of Separation Science, 2007, v. 30, pp. 1082-1087).
Ostman et al., "Tolerosome-Induced Oral Tolerance is MHC Dependent", Immunology, vol. 116, pp. 464-476 (2005).
Pan et al., "Fate of the Transferrin Receptor During Maturation of Sheep Reticulocytes in Vitro: Selective Externalization of the Receptor", Cell, vol. 33, pp. 967-977 (Jul. 1983).
Pandey et al., "An Update in Recurrent Spontaneous Abortion", Archives of Gynecology and Obstetrics, vol. 272, pp. 95-108 (2005).
Patel et al., "Multipotent Menstrual Blood Stromal Stem Cells: Isolation, Characterization, and Differentiation", Cell Transplantation, vol. 17, pp. 303-311 (2008).
Peche et al., "Induction of Tolerance by Exosomes and Short-Term Immunosuppression in a Fully MHC-Mismatched Rat Cardiac Allograft Model", American Journal of Transplantation, vol. 6, pp. 1541-1550 (2006).
Popov et al., "Preventing Autoimmune Arthritis Using Antigen-Specific Immature Dendritic Cells: a novel tolerogenic vaccine", Arthritis research & therapy, 8(5), R141—pp. 1-11 (2006).
Qazi et al., "Antigen-loaded exosomes alone induce Th1-type memory through a B-cell-dependent mechanism", Blood, vol. 113, No. 12, pp. 2673-2683 (2009).
Ra et al., "Stem Cell Treatment for Patients with Autoimmune Disease by Systemic Infusion of Culture-Expanded Autologous Adipose Tissue Derived Mesenchymal Stem Cells", Journal of Translational Medicine, 9, pp. 181-192 (2011).
Rao, "Conserved and Divergent Paths that Regulate Self-Renewal in Mouse and Human Embryonic Stem Cells", Developmental Biology, vol. 275, pp. 269-286 (2004).
Raposo et al., "B Lymphocytes Secrete Antigen-presenting Vesicles", The Journal of Experimental Medicine, vol. 183, pp. 1161-1172 (Mar. 1996).
Ruffner et al., "B7-1/2, but not PD-LI/2 Molecules, are Required on IL-10-Treated Tolerogenic DC and DC-Derived Exosomes for in Vivo Function", European Journal of Immunology, 39(11), pp. 3084-3090 (2009).
Sabapatha et al.,"Specific Isolation of Placenta-Derived Exosomes From the Circulation of Pregnant Women and their Immunoregulatory Consequences", American Journal of Reproductive Immunology, vol. 56, pp. 345-355 (2006).
Sato et al., "Molecular Signature of Human Embryonic Stem Cells and its Comparison wWth the Mouse", Developmental Biology, vol. 260, pp. 404-413 (2003).
Schwab et al., "Identification of Surface Markers for Prospective Isolation of Human Endometrial Stromal Colony-Forming Cells", Human Reproduction, 23(4), pp. 934-943 (2008).
Segura et al., "Mature Dendritic Cells Secrete Exosomes With Strong Ability to Induce Antigen-Specific Effector Immune Responses", Blood Cells, Molecules & Diseases, vol. 35, pp. 89-93 (2005).
Silverman et al., "Exosomes and Other Microvesicles in Infection Biology: organelles with unanticipated phenotypes", Cellular Microbiology, 13(1), pp. 1-9 (2011).
Stamm et al., "Stem Cell Therapy for Ischemic Heart Disease: beginning or end of the road", Cell Transplant, vol. 15 Suppl. 1, pp. S47-S56, (2006)—Abstract Only.
Sun et al., "Mesenchymal Stem Cell Transplantation Reverses Multiorgan Dysfunction in Systemic Lupus Erythematosus Mice and Humans", Stem Cells, 27(6), pp. 1421-1432 (2009).
Szajnik et al., "Tumor-Derived Microvesicles Induce, Expand and Up-Regulate Biological Activities of Human Regulatory T Cells (Treg)", PloS ONE, 5(7), pp. 1-10—e11469 (2010).
Tang et al.,"Comparison of isolation methods of exosomes and exosomal RNA from cell culture medium and serum," International Journal of Molecular Medicine, vol. 40, 2017, pp. 834-844.
Taylor et al. "Pregnancy-Associated Exosomes and their Modulation of T Cell Signaling", Journal of Immunology,vol. 176, pp. 1534-1543 (2006).
Taylor et al., "Tumour-Derived Exosomes and Their Role in Cancer-Associated T-Cell Signalling Defects", British Journal of Cancer, vol. 92, pp. 305-311 (2005).
Thery et al., "Membrane Vesicles as Conveyors of Immune Responses", Nature Reviews—Immunology, vol. 9, pp. 581-593 (2009).
Uccelli et al., Why Should Mesenchymal Stem Cells (MSCs) Cure Autoimmune Diseases? Current Opinion in Immunology, vol. 22, pp. 768-774 (2010).
Valenti et al., "Tumor-Released Microvesicles as Vehicles of Immunosuppression", Cancer Research, 67(7): pp. 2912-2915 (2007).
Verfaillie, "Adult Stem Cells: Assessing the Case for Pluripotency", TRENDS in Cell Biology, 12(11), pp. 502-508 (2002).
Viaud et al., "Updated Technology to Produce Highly Immunogenic Dendritic Cell-Derived Exosomes of Clinical Grade: a critical role of interferon-gamma", Journal of Immunotherapy, 34(1), pp. 65-75 (2011).
Wei et al., "A Multicenter, Double-Blind, Randomized, Controlled Phase III Clinical Trial of Chicken Type II Collagen in Rheumatoid Arthritis", Arthritis Research & Therapy, 11(6), pp. R180—1-10 (2009).
Weiner et al., "Oral tolerance", Immunological reviews, 241(1), pp. 241-259 (2011).
Wu et al., "Cell Delivery in Cardiac Regenerative Therapy", Ageing Research Reviews, vol. 11, pp. 32-40 (2012).
Yang et al., "Exosomes Derived from Immature Bone Marrow Dendritic Cells Induce Tolerogenicity of Intestinal Transplantation in Rats", The Journal of Surgical Research, vol. 171, pp. 826-832 (2011).
Yang et al., "Human Umbilical Cord Blood-Derived Mononuclear Cell Transplantation: case series of 30 subjects with hereditary ataxia", Journal of Translational Medicine, vol. 9, pp. 65-69 (2011).
Zhang et al., "CD4(+) T Cell-Released Exosomes Inhibit CD8(+) Cytotoxic T-Lymphocyte Responses and Antitumor immunity", Cellular & Molecular Immunology, vol. 8, pp. 23-30 (2011).

FIGURE 1

THERAPEUTIC IMMUNE MODULATION BY STEM CELL SECRETED EXOSOMES

CROSS-REFERENCE TO RELATED APPLICATIONS

This application is a continuation of U.S. patent application Ser. No. 15/228,036, filed Aug. 4, 2016, now abandoned, which is a continuation application of U.S. patent application Ser. No. 13/756,310, filed Jan. 31, 2013 (now U.S. Pat. No. 9,427,450, issued Aug. 30, 2016), which claims the benefit under 35 U.S.C. § 119 to Provisional Application Ser. No. 61/592,636 filed Jan. 31, 2012, the entirety of which is hereby incorporated by reference.

FIELD OF THE INVENTION

The invention pertains to the field of immune modulation, specifically, the invention relates to immune modulation via administration of microvesicular particles derived from cells with regenerative potential such as stem cells. More specifically, the invention pertains to inhibition of autoimmunity, transplant rejection, inflammation, and graft versus host disease through administration of exosomes.

BACKGROUND OF THE INVENTION

Exosomes are nano-size particles between 40-100 nm in size originally identified as a byproduct of reticulocyte maturation. Exosomes have been described from numerous cell types including tumors, platelets, and immune cells such as dendritic cells. The role of exosomes in immune modulation has been historically restricted to the area of dendritic cell exosomes, which are known to carry MHC molecules, antigens, and both costimulatory and co-inhibitory molecules. The majority of work in the area of exosome immune modulation has focused on stimulation of immunity, particularly in the area of cancer, in which exosome-based vaccines have been developed and entered clinical trials.

Very recently, exosomes have been identified in conditioned media of various stem cell populations including mesenchymal stem cells, and CD34 cells. These exosomes have been studied as "trophic factors" and stimulators of angiogenesis.

However to date, the use of exosomes derived from stem cells for immune modulation has not been performed. Mesenchymal stem cells possess advantages to DC or other immune cells in that they can be generated in large quantities, that their membrane products have an affinity towards the draining lymph node, and that they possess other known regenerative activities.

It is the scope of the current invention to overcome limitations of DC-exosome based immune modulation through the use of MSC.

SUMMARY OF THE INVENTION

The current invention provides methods of inducing immune modulation in a mammal through administration of exosomes derived from stem cell populations. In one aspect of the invention, exosomes are derived from bone marrow mesenchymal stem cells. In another aspect, exosomes are isolated from culture of endometrial regenerative cells (ERC). Exosomes may be used to induce specific or non-specific tolerance. In one embodiment, exosomes are used to facilitate acceptance of an organ or tissue. In another embodiment, exosomes are derived from ERC that are used for therapeutic use and exosomes from the same donor are administered along with ERC for treatment of an individual in need of treatment.

Further methods include neuronal stem cells selected based on expression of one or more of the following antigens: RC-2, 3CB2, BLB, Sox-2hh, GLAST, Pax 6, nestin, Muashi-1, NCAM, A2B5 and prominin. Further methods include circulating peripheral blood stem cells characterized by ability to proliferate in vitro for a period of over 3 months. Further methods include circulating peripheral blood stem cells characterized by expression of CD34, CXCR4, CD117, CD113, and c-met. Further methods include circulating peripheral blood stem cells that lack substantial expression of differentiation associated markers. Further methods include differentiation associated markers selected from a group comprising of CD2, CD3, CD4, CD11, CD11a, Mac-1, CD14, CD16, CD19, CD24, CD33, CD36, CD38, CD45, CD56, CD64, CD68, CD86, CD66b, and HLA-DR.

Further embodiments encompass methods wherein mesenchymal stem cells express one or more of the following markers: STRO-1, CD105, CD54, CD106, HLA-I markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD10, CD13, STRO-2, VCAM-1, CD146, and THY-1. Further embodiments encompass methods wherein mesenchymal stem cells do not express substantial levels of HLA-DR, CD117, and CD45. Further embodiments encompass methods wherein mesenchymal stem cells are derived from a group selected from: bone marrow, adipose tissue, umbilical cord blood, placental tissue, peripheral blood mononuclear cells, differentiated embryonic stem cells, and differentiated progenitor cells. Further embodiments encompass methods wherein germinal stem cells express markers selected from a group comprising of: Oct4, Nanog, Dppa5 Rbm, cyclin A2, Tex18, Stra8, Daz1, beta1- and alpha6-integrins, Vasa, Fragilis, Nobox, c-Kit, Sca-1 and Rex1. Further embodiments encompass methods wherein adipose tissue derived stem cells express markers selected from a group consisting of: CD13, CD29, CD44, CD63, CD73, CD90, CD166, Aldehyde dehydrogenase (ALDH), and ABCG2. Further embodiments encompass methods wherein adipose tissue derived stem cells are a population of purified mononuclear cells extracted from adipose tissue capable of proliferating in culture for more than 1 month. Further embodiments encompass methods wherein exfoliated teeth derived stem cells express markers selected from the group consisting of: STRO-1, CD146 (MUC18), alkaline phosphatase, MEPE, and bFGF.

Further embodiments encompass methods wherein hair follicle stem cells express markers selected from a group comprising of: cytokeratin 15, Nanog, and Oct-4. Further embodiments encompass methods wherein hair follicle stem cells are capable of proliferating in culture for a period of at least one month. Further embodiments encompass methods wherein hair follicle stem cells secrete one or more of the following proteins when grown in culture: basic fibroblast growth factor (bFGF), endothelin-1 (ET-1) and stem cell factor (SCF).

Further embodiments encompass methods wherein dermal stem cells express markers selected from a group comprising of: CD44, CD13, CD29, CD90, and CD105. Further embodiments encompass methods wherein dermal stem cells are capable of proliferating in culture for a period of at least one month. Further embodiments encompass methods wherein parthenogenically derived stem cells are generated by addition of a calcium flux inducing agent to activate an oocyte followed by enrichment of cells expressing markers selected from a group comprising of SSEA-4, TRA 1-60 and TRA 1-81.

Further embodiments encompass methods wherein reprogrammed stem cells are selected from a group comprising of: cells subsequent to a nuclear transfer, cells subsequent to a cytoplasmic transfer, cells treated with a DNA methyltransferase inhibitor, cells treated with a histone deacetylase inhibitor, cells treated with a GSK-3 inhibitor, cells induced to dedifferentiate by alteration of extracellular conditions, and cells treated with various combination of the mentioned treatment conditions. Further embodiments encompass methods wherein nuclear transfer comprises introducing nuclear material to a cell substantially enucleated, said nuclear material deriving from a host whose genetic profile is sought to be dedifferentiated.

Further embodiments encompass methods wherein cytoplasmic transfer comprises introducing cytoplasm of a cell with a dedifferentiated phenotype into a cell with a differentiated phenotype, such that said cell with a differentiated phenotype substantially reverts to a dedifferentiated phenotype. Further embodiments encompass methods wherein DNA demethylating agent is selected from a group comprising of: 5-azacytidine, psammaplin A, and zebularine. Further embodiments encompass methods wherein histone deacetylase inhibitor is selected from a group comprising of: valproic acid, trichostatin-A, trapoxin A and depsipeptide. Further embodiments encompass methods wherein cells are identified based on expression multidrug resistance transport protein (ABCG2) or ability to efflux intracellular dyes such as rhodamine-123 and or Hoechst 33342. Further embodiments encompass methods wherein cells are derived from tissues such as pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue.

Further embodiments encompass methods wherein committed progenitor cells are selected from a group comprising of: endothelial progenitor cells, neuronal progenitor cells, and hematopoietic progenitor cells. Further embodiments encompass methods wherein committed endothelial progenitor cells are purified from the bone marrow. Further embodiments encompass methods wherein committed endothelial progenitor cells are purified from peripheral blood. Further embodiments encompass methods wherein committed endothelial progenitor cells are purified from peripheral blood of a patient whose committed endothelial progenitor cells are mobilized by administration of a mobilizing agent or therapy. Further embodiments encompass methods wherein stem cells are cultured in a three-dimensional bioreactor. Further embodiments encompass methods wherein stem cells are induced to produce an increased amount of exosomes. Further embodiments encompass methods wherein induction of exosomes from said stem cells is achieved by treatment of said stem cells with cytokines. Further embodiments encompass methods wherein exosomes are concentrated by a means selected from: a) ultracentrifugation; b) column chromatography; c) size exclusion; d) filtration through a device containing an affinity matrix selective towards exosomes. Further embodiments encompass methods wherein exosomes generated from said stem cells are used to inhibit inflammation in an injured tissue. Further embodiments encompass methods wherein exosomes are transfected with a genetic material so as to allow delivery of said genetic material to an immune cell. Further embodiments include methods of treating an autoimmune condition through administration of a population of stem cell exosomes capable of suppressing a biological pathway associated with an immune pathway associated with said autoimmune condition.

Further embodiments encompass methods wherein an autoimmune condition is selected from a group comprising of: a) diabetes; b) multiple sclerosis; c) rheumatoid arthritis; d) Hashimoto's thyroiditis; e) graft rejection; and f) graft versus host disease. Further embodiments include methods of treating an autoimmune condition comprising incorporating one or more autoantigens into said exosomes generated from said stem cells, with incorporation of said autoantigen being accomplished by introduction into said stem cell or introduction into said exosome generated by said stem cell and administering said exosomes into a patient in need thereof. Further embodiments encompass methods of treating an autoimmune condition in a mammal comprising administering exosomes derived from stem cells that have been transfected one or more autoantigens representing said autoimmune condition. Further embodiments encompass methods wherein exosomes are derived from embryonic stem cells. Further embodiments encompass methods wherein exosomes are derived from mesenchymal stem cells. Further embodiments encompass methods of treating an autoimmune condition comprising of: a) obtaining a mesenchymal stem cell; b) introducing into said mesenchymal stem cell an antigen, in a manner such that said antigen is introduced into said mesenchymal stem cell in a manner so that said antigen is incorporated by said mesenchymal stem cell such that said antigen enters the exosomes that are released by said mesenchymal stem cell; c) purifying said antigen bearing exosomes; and d) administering said antigen-expressing exosomes into a patient in need of therapy. Further embodiments encompass methods wherein a mesenchymal stem cell is selected from a group of mesenchymal stem cells selected from a group comprising of: a) a bone marrow mesenchymal stem cell; b) an adipose derived mesenchymal stem cell; c) a dental pulp derived mesenchymal stem cell; d) a fallopian tube derived mesenchymal stem cell; e) an endometrial regenerative cell; f) a peripheral blood derived mesenchymal stem cell; g) a cord blood derived mesenchymal stem cell; h) a placental derived mesenchymal stem cell; i) a Wharton's Jelly derived mesenchymal stem cell; k) a menstrual blood derived mesenchymal stem cell; and l) an endometrial derived mesenchymal stem cell. Further embodiments encompass methods wherein ERCs are cultured in a DMEM F12 media in approximately 10% fetal calf serum for a period of 1-100 hours.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE PREFERRED EMBODIMENT

Exosomes are nanoparticles (40-100 nm) in size that possess highly defined homogeneous characteristics [1]. Originally thought to be a by-product of cell protein turnover [2], these particles are becoming appreciated as a critical means of intracellular communication in areas ranging from neurotransmission [3], to immune modulation [2], to infectious disease [4]. Compared with other secreted vesicles, exosomes have much better defined biophysical and biochemical properties, specifically, they have a diameter of 40-100 nm (with a density in sucrose of 1.13-1.19 g/ml, and can be sedimented at 100,000 g [1]. Their membranes are enriched in cholesterol, sphingomyelin and ceramide, and are known to contain lipid rafts. Exosomes were originally discovered as a means of exportation of the transferrin receptor during sheep reticulocyte maturation [5]. In recent years an explosion of interest in exosomes has occurred, with a wide variety of cells being reported to secrete these nanoparticles ranging from T cells [6, 7], B cells [8, 9], dendritic cells [10, 11], tumor cells [12, 13], neurons [14, 15], oligodendrocytes [16], and placental cells [17]. It is believed that exosomes play fundamental role in immune escape of the "fetal allograft" [18]. Endometrial regenerative cells (ERC) are believed to be precursors of MSC that development into the maternal portion of the placenta. Given the high angiogenic activity of ERC, as well as their ability to induce therapeutic effects in xenogeneic immune competent models [19], one embodiment of the invention is the utilization of ERC exosomes as a non-cellular method of inducing immune modulatory effects that are present when ERC are administered therapeutically. In another embodiment, exosomes from other stem cells may be utilized for immunotherapeutic purposes.

Immunological functions of exosomes were first identified in B cells [20], through studies demonstrating that these cells contain a late endocytic compartment, called MIIC (major histocompatibility complex MHC class II-enriched compartment), that harbors newly, synthesized MHC class II molecules in transit to the plasma membrane. It was found that the MIIC compartment would fuse with the plasma membrane, but instead of the MHC II molecules becoming membrane bound, some would be found in the soluble fraction. These particles, which the investigators termed "exosomes" in reference to original work on reticulocytes [5], were demonstrated to possess a distinct surface composition as compared to the plasma membrane. Interestingly, in the exosomes, a high concentration of MHC I and II, as well as antigen were found. In 2004 our group filed Canadian Patent #2453198 entitled "QUANTIFICATION AND GENERATION OF IMMUNE SUPPRESSIVE EXOSOMES". To our knowledge these were the first data demonstrating that in certain contexts, exosomes may suppress the immune system. These data, which were subsequently published, demonstrated that exosomes from prostate cancer patients suppress T cell activation in an MHC I and Fas ligand dependent manner [21]. In one embodiment of the invention, methodologies used for purification of immune suppressive exosomes from tumor cells, incorporated by reference, are applied to conditioned media of stem cells, specifically of mesenchymal stem cells, and more specifically of endometrial regenerative cells, in order to isolate, concentrate and therapeutically administer exosomes derived from stem cells for immune modulatory purposes.

We have previously published that immature dendritic cells promote induction of tolerance [22], and that administration of this "tolerogenic vaccine" is capable of suppressing autoimmunity in an in vivo manner [23]. Given the notion that mature dendritic cell exosomes are immune stimulatory [24, 25], it was logical to investigate whether exosomes generated from "tolerogenic" dendritic cells may prevent immune activation. Indeed Ruffner et al. demonstrated that dendritic cells treated with IL-10 to block maturation secreted exosomes that inhibited immune response in an antigen-specific manner in the delayed type hypersensitivity system [26]. Furthermore, they demonstrated that the immune inhibiting effect of the IL-10-treated exosome required presence of CD80 and CD86 on the exosome. Yang et al used donor-strain derived exosomes from immature dendritic cells to enhance allograft survival in a F334>Wistar intestinal allotransplantation model [27]. The researchers demonstrated that as little as 20 ug of donor (but not recipient) derived exosomes was capable of causing a more than double increase in graft survival. Similar prolongation of graft survival using donor immature dendritic cell isolated exosomes was observed in a cardiac allograft model by another group [28]. Kim et al demonstrated that exosomes mediating effects of tolerogenic DC were on average 75 nm in size [29] and depended on FasL for mediation of suppressive effects on T cells using KLH recall response as an output assay. Exosome production from tolerogenic dendritic cells may be labeled by some as "artifactual", therefore, let us examine the relevance of exosomes in naturally-occurring examples of immunological tolerance. In one embodiment of the invention, techniques used to enhance immune suppressive activities of exosomes secreted by other cells are applied to stem cells, mesenchymal stem cells and endometrial regenerative cells in order to augment immune suppressive activities. For example, ERC may be treated with compounds that inhibit inflammatory signals, such as IL-10, in order to generate populations of ERC that produce exosomes with enhanced immune modulatory activities. Conversely, in other aspects of the invention, exosomes may be purified from ERC that are growing under standard culture conditions.

The term "fetal allograft" has been often used to refer to the ability of the genetically mismatched fetus to survive within the mother. Although the fetal maternal barrier was originally believed to act as a barrier to trans-placental traffic, this was later found to be erroneous. Murine embryo transfer experiments utilizing wild-type embryos transferred into pseudopregnant LacZ mothers demonstrated extensive maternal cell infiltration, persisting into adulthood [30]. Conversely fetal cells have been demonstrated to enter maternal circulation and play both therapeutic [31] and pathological roles [32] depending on context. It has become apparent that during pregnancy, local and systemic immune deviation occurs [33], and that failure to induce this "natural immune modulation" is associated with recurrent spontaneous abortions [34, 35]. It appears that exosome production is associated, at least in part, with reprogramming of the maternal immune system to accommodate the allogeneic fetus. In 2005, Frängsmyr et al. reported that fetal syncytiotrophoblast cells express intracellular Fas ligand (FasL), which is secreted as exosomal particles into systemic circulation. They also found similar FasL expressing exosomes to be generated by cultured trophoblast cells [36]. As mentioned above in the examples of cancer-derived exosomes, and tolerogenic dendritic cell derived exosomes, FasL expression on these particles is associated with killing of activated T cells. Therefore, it may be conceptually possible that in physiological situations in which tolerogenesis is required, exosomes bearing antigen on MHC I/II, with or without costimulation, transmit a signal to the T cells that activate them antigen-specifically. The activated T cell then receives a "death signal" from the FasL, causing specific killing of the T cell clones that pose a threat to the exosome-producing entity. A functional association between FasL expression, exosome concentration, and suppression of T cell activity as assessed by TCR-zeta chain activity was demonstrated in Doug Taylor's group. Furthermore, they observed that preterm deliveries, which are associated with higher degree of maternal-antifetal immunity are associated with lower concentrations of FasL expressing exosomes [37]. Pregnancy-associated exosomes appear to possess multiple means of modulating T cell responses. For example, the same group demonstrated that the "co-inhibitory" molecule PD1 ligand, is also expressed on pregnancy derived exosomes in circulation and that the inhibition of T cell activity was occurring not only at the CD4 level but more profoundly on CD8 T cells [38]. Another group demonstrated that pregnancy-associated exosomes, and those isolated from syncytiotrophoblasts express high levels of MHC class I chain-related proteins A and B (MICA/B) [18]. This protein specifically binds to the natural killer activating receptor NKG2D and suppresses NK activity. Interestingly it was found that culture of peripheral blood mononuclear cells from non-pregnant women with exosomes from pregnant women resulted in downregulation of NKG2D expression, as well as suppressed NK activity. Additionally, pregnant women had substantially lower expression of NKG2D compared to non-pregnant controls. The same group subsequently found that pregnancy-associated exosomes express a second family of human NKG2D ligands, the UL-16 binding proteins (ULBP), which inhibit not only NK cell activity, but also CD8 T cells and gamma delta T cells [39]. The potent immune modulation associated with pregnancy has been reported to inhibit clinical autoimmunity in conditions such as rheumatoid arthritis, [40] and multiple sclerosis [41]. Interestingly, a study in the animal model of multiple sclerosis, experimental autoimmune encephalomyelitis, demonstrated that exosomes produced during pregnancy may be responsible for the therapeutic effects on autoimmunity [42]. Thus in the situation of "natural tolerance" induced by pregnancy, it appears that exosomes play a role in temporary downmodulation of maternal responses. The potential of tumor-derived exosomes to kill/inactivate T cells through a Fas-FasL mechanism has been demonstrated in ovarian cancer [43], prostate cancer [21], and melanoma [7]. However, numerous other means of immune modulation have been ascribed to cancer-derived exosomes. For example, Valenti et al showed that exosomes from melanoma and cervical cancer patients can "reprogram" monocytes into myeloid derived suppressor cells [44]. These cells play an important role in protecting tumor cells from T cell mediated immunity through secretion of suppressive factors such as PGE2, nitric oxide, arginase, and production of reactive oxygen intermediates [45]. Another "indirect" means by which tumor exosomes contribute to immune evasion is through the generation of T regulatory cells [46]. It was recently demonstrated by Whiteside's group that co-culture of tumor derived exosomes with naïve T cells, under certain conditions, would lead to potent generation of T regulatory cells that could suppress other T cells from activation. This concept of "infectious tolerance" has been described in the area of tumor immunotherapy with little mechanistic knowledge. Yet another mechanism of tumor exosome immune suppression is through the production of free adenosine via the enzyme CD73, which has been demonstrated to be expressed highly on tumor-derived exosomes 12. Induction of oral tolerance appears to be associated with generation of T regulatory/Th3 cells that are specific to food-borne antigens [47]. While clinical trials of oral tolerance in rheumatoid arthritis [48], and multiple sclerosis [49, 50], have shown some promising results, to date, efficacy has not been able to meet the bar required by regulators for registration. By understanding biological mechanisms involved in induction of this innocuous form of tolerance, it may be feasible to develop therapeutic modalities to increase efficacy. It was demonstrated that subsequent to feeding with a nominal antigen, plasma-circulating exosomes containing MHC II and the antigen could be captured. In vitro culture of these exosomes revealed ability to antigen-specifically suppress T cell activation [51]. Using a murine allergy model it was demonstrated that protection from allergy could be transferred via exosomes collected from mice that had been fed the allergen orally [52]. These data suggest that tolerance induction may be occurring through the generation of tolerogenic exosomes as had been seen in the case of pregnancy and cancer in the previous sections. In certain embodiments of the invention, exosomes from stem cells are purified based on expression of certain markers that have been associated with naturally-occurring immune suppression induced by exosomes secreted by non-stem cells. In one embodiment, exosomes are generated in a means that causes preferential production of CD73 expressing exosomes. Specifically, ERC are cultured under conditions optimized for production of CD73 expressing exosomes by variation of culture conditions. In one specific embodiment, 10 ng/ml of IL-10 is added to ERC in tissue culture. Culture of ERC has been described in the paper Meng et al [53], and incorporated by reference. Specific culture conditions and clinical use of ERC has been previously described in conditions such as congestive heart failure 54 and spinal cord injury [55]. Additionally, other cells may be used as a source of stem cells capable of producing exosomes. Cord blood cells useful for therapeutic applications have been described by us and are incorporated by reference [56].

Mesenchymal stem cells (MSC) are a family to which the ERC belong to. It has been reported that MSC express numerous immune modulatory/suppressive properties. For example, it has been demonstrated that MSC are therapeutically useful in clinical trials of immune-based conditions such as graft versus host disease [57], systemic lupus erythematosus [58], multiple sclerosis [59], and rheumatoid arthritis [60]. While it has previously been demonstrated that MSC-secreted exosomes are angiogenic and possess therapeutic activity in animal infarct models [61], the current invention is distinct from prior uses in that exosomes are utilized to elicit immune modulation. The possibility that MSC-derived exosomes are immune modulatory bring about several drug development options. For exosomes, exosomes have been engineered to act as vectors for siRNA, unfortunately, to date only dendritic cell exosomes have been used for this purpose [62]. Given that dendritic cells are inherently immunogenic, and difficult to expand in great quantities due to their terminal nature, the current invention overcomes this by providing a source of exosomes that is capable of generation in large numbers.

In one embodiment of the invention, exosomes are generated from ERC that are genetically compatible with ERC administered for the purpose of cell therapy. In one specific embodiment, a master cell bank is generated from one ERC donor. During the process of ERC generation, exosomes are collected from tissue culture media and concentrated using methods known in the art. Specific methodologies include ultracentrifugation, HPLC, adherence to substrate based on affinity, or filtration based on size exclusion. Exosomes collected are administered systemically to patients receiving ERC therapeutically in order to enhance engraftment of ERC. In other embodiments, ERC derived exosomes are used either as a monotherapy, or a combination therapy with other immune modulatory interventions in order to augment immune modulatory activities of said therapy.

Example 1: ERC Exosomes Inhibit MLR and Augment ERC Ability to Inhibit MLR

Exosome Purification. Exosomes were prepared from the cell culture supernatant of day 4 ERC cultures by differential centrifugation. Briefly, recovered culture supernatant was subjected to three successive centrifugations at 300 g (5 min), 1,200 g (20 min), and 10,000 g (30 min) to eliminate cells and debris, followed by centrifugation for 1 h at 100,000 g. To remove excess serum proteins, the exosome pellet was washed with a large volume of PBS, centrifuged at 100,000 g for 1 h, and finally resuspended in 120 ul of PBS for further studies. The exosomes were quantified by a micro Bradford protein assay (Bio-Rad). Each batch was standardized by protein content, Fetal calf serum exosomes were prepared using the same method.

Figure 1:
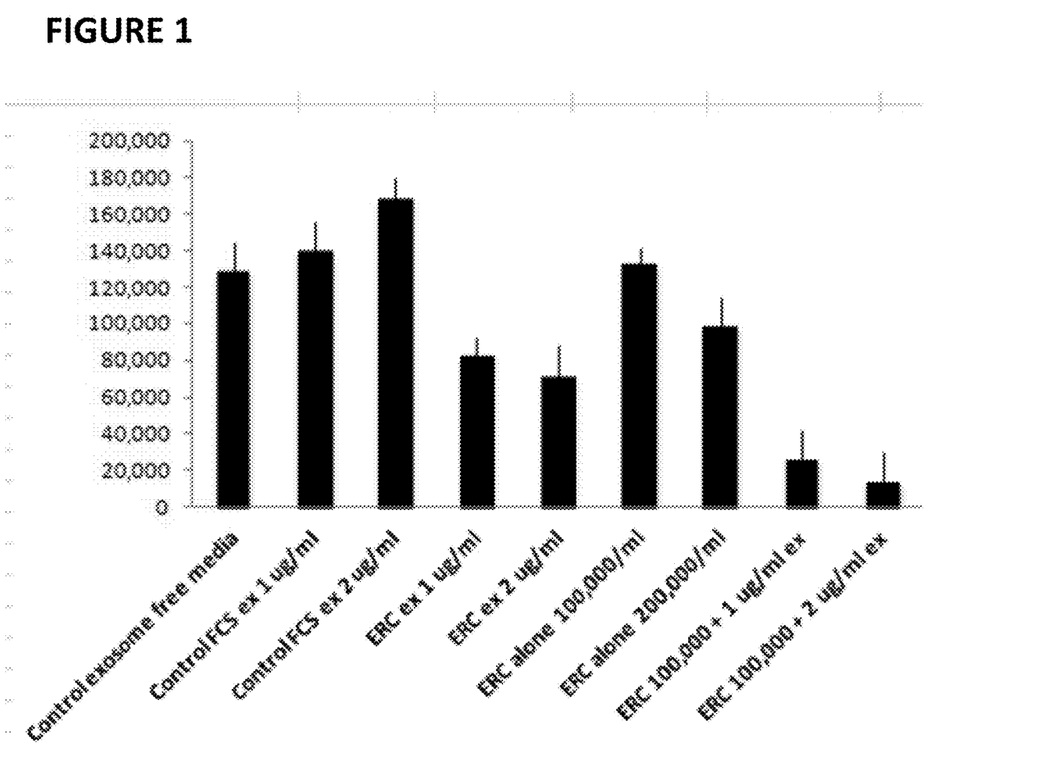
FIG. 1 is a bar graph showing various cell cultures ability to inhibit MLR
Figure 2:
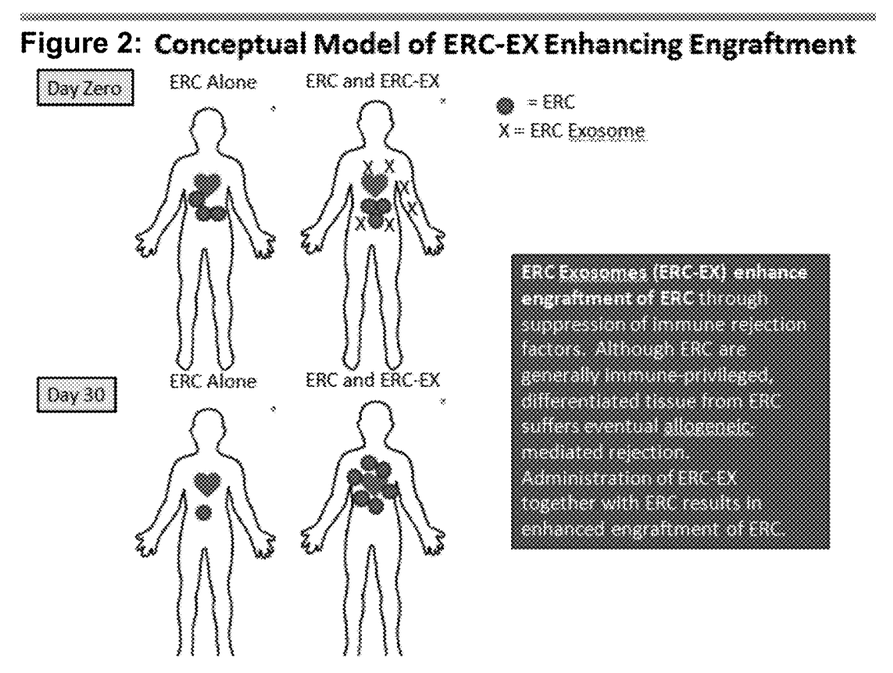
FIG. 2 is a conceptual model of ERX-EX Enhancing Engraftment.

Tissue Culture Peripheral blood mononuclear cells (PBMC) were isolated from 5 ml of blood by Ficoll density gradient (Sigman-Aldrich) utilizing two HLA-incompatible donors. Cells were washed twice in phosphate buffered saline (PBS) and plated in round-bottom, 96-well plates (Nunc). In each well, 500,000 PBMC from each donor were added to a total volume of 200 uL in RPMI media containing 10% fetal calf serum (Life Technologies). In all cultures the media was centrifuged for 3 h at 100,000 g to deplete of exosomes. Additionally, exosomes and/or ERC were added as described in the FIG. 1. On day 4, 1 uCi of [3H]thymidine was added to each well 16 h before harvest. Radioactive labeling of proliferating T cells was measured on a microplate beta counter (Wallac). Data in FIG. 1 demonstrate that adding of 200×103 ERC to MLR inhibited T cell proliferation by 24% p<0.05 compared to control. Interestingly, addition of 1-2 ps of purified ERC exosomes (ERC ex) inhibited MLR significantly better. Much more importantly, adding to MLR cultures 100×103 ERC with 1-2 ps ERC ex significantly enhance immune inhibition.

Example 2: ERC Exosomes Enhance In Vivo Engraftment of ERC in Immune Competent BALB/c Mice The previous experiments suggest that addition of ERC-Exosomes to a mixed lymphocyte reaction (MLR) enhances ability of the ERC cell to decrease ongoing immune response in vitro. Accordingly, we sought to determine whether co-administration of exosomes may enhance engraftment of ERC. As seen in Table 1, administration of 40 and 80 micrograms of ERC-Exosomes per mouse was sufficient to significantly enhance ERC engraftment.

TABLE 1

Adminstation of ERC-EX Increases Human ERC Engraftment in Innume Competent BALB/c Mice

| Treatment | 1 hr | 7 days | 14 days | 30 days |
|---|---|---|---|---|
| ERC* | 28 (±5)[#] | 2 (±1) | 0 (±1) | 0 (±0) |
| ERC + 10 ug ERC-EX | 32 (±7) | 5 (±4) | 4 (±3) | 3 (±3) |
| ERC + 20 ug ERC-EX | 25 (±9) | 18 (±4) | 6 (±5) | 4 (±1) |
| ERC + 40 ug ERC-EX | 26 (±5) | 22 (±1) | 19 (±2) | 17 (±3) |
| ERC + 80 ug ERC-EX | 33 (±3) | 24 (±4) | 25 (±4) | 19 (±5) |

*ERC were administered into the gastrocnemius muscle at a concentration of 100,000 cells.
[#]Detection of human cells was performed using mouse anti-human CD44 Thermo Scientific, Clone 156-3C11) and secondary antibody, anti-mouse IgG2a (Lab Vision, NC-1390), immunoflourescence of Alexa was detected. Numbers represent cells per microscope viewing field at 200X magnification in a total of 5 slides. Mice were sacrificed at the indicated days.

REFERENCES

All References, Patents and Patent Applications referenced herein are expressly incorporated by reference in their entireties.

1. Thery, C., M. Ostrowski, and E. Segura, Membrane vesicles as conveyors of immune responses. Nature reviews. Immunology, 2009. 9(8): p. 581-93.
2. Ludwig, A. K. and B. Giebel, Exosomes: Small vesicles participating in intercellular communication. The international journal of biochemistry & cell biology, 2011.
3. Alvarez-Erviti, L., et al., Lysosomal dysfunction increases exosome-mediated alpha-synuclein release and transmission. Neurobiology of disease, 2011. 42(3): p. 360-7.
4. Silverman, J. M. and N. E. Reiner, Exosomes and other microvesicles in infection biology: organelles with unanticipated phenotypes. Cellular microbiology, 2011. 13(1): p. 1-9.
5. Pan, B. T. and R. M. Johnstone, Fate of the transferrin receptor during maturation of sheep reticulocytes in vitro: selective externalization of the receptor. Cell, 1983. 33(3): p. 967-78.
6. Alonso, R., et al., Diacylglycerol kinase alpha regulates the formation and polarisation of mature multivesicular bodies involved in the secretion of Fas ligand-containing exosomes in T lymphocytes. Cell death and differentiation, 2011. 18(7): p. 1161-73.
7. Zhang, H., et al., CD4(+) T cell-released exosomes inhibit CD8(+) cytotoxic T-lymphocyte responses and antitumor immunity. Cellular & molecular immunology, 2011. 8(1): p. 23-30.
8. Mathews, J. A., et al., CD23 Sheddase A disintegrin and metalloproteinase 10 (ADAM10) is also required for CD23 sorting into B cell-derived exosomes. The Journal of biological chemistry, 2010. 285(48): p. 37531-41.
9. Buschow, S. I., et al., MHC class II-associated proteins in B-cell exosomes and potential functional implications for exosome biogenesis. Immunology and cell biology, 2010. 88(8): p. 851-6.
10. Hwang, I. and D. Ki, Receptor-mediated T cell absorption of antigen presenting cell-derived molecules. Frontiers in bioscience: a journal and virtual library, 2011. 16: p. 411-21.
11. Viaud, S., et al., Updated technology to produce highly immunogenic dendritic cell-derived exosomes of clinical grade: a critical role of interferon-gamma. Journal of immunotherapy, 2011. 34(1): p. 65-75.

12. Clayton, A., et al., Cancer exosomes express CD39 and CD73, which suppress T cells through adenosine production. Journal of immunology, 2011. 187(2): p. 676-83.
13. Battke, C., et al., Tumour exosomes inhibit binding of tumour-reactive antibodies to tumour cells and reduce ADCC. Cancer immunology, immunotherapy: CII, 2011. 60(5): p. 639-48.
14. Lachenal, G., et al., Release of exosomes from differentiated neurons and its regulation by synaptic glutamatergic activity. Molecular and cellular neurosciences, 2011. 46(2): p. 409-18.
15. Faure, J., et al., Exosomes are released by cultured cortical neurones. Molecular and cellular neurosciences, 2006. 31(4): p. 642-8.
16. Fitzner, D., et al., Selective transfer of exosomes from oligodendrocytes to microglia by macropinocytosis. Journal of cell science, 2011. 124(Pt 3): p. 447-58.
17. Mincheva-Nilsson, L. and V. Baranov, The role of placental exosomes in reproduction. American journal of reproductive immunology, 2010. 63(6): p. 520-33.
18. Mincheva-Nilsson, L., et al., Placenta-derived soluble MHC class I chain-related molecules down-regulate NKG2D receptor on peripheral blood mononuclear cells during human pregnancy: a possible novel immune escape mechanism for fetal survival. Journal of immunology, 2006. 176(6): p. 3585-92.
19. Murphy, M. P., et al., Allogeneic endometrial regenerative cells: an "Off the shelf solution" for critical limb ischemia? Journal of translational medicine, 2008. 6: p. 45.
20. Raposo, G., et al., B lymphocytes secrete antigen-presenting vesicles. The Journal of experimental medicine, 1996. 183(3): p. 1161-72.
21. Abusamra, A. J., et al., Tumor exosomes expressing Fas ligand mediate CD8+ T-cell apoptosis. Blood cells, molecules & diseases, 2005. 35(2): p. 169-73.
22. Ichim, T. E., R. Zhong, and W. P. Min, Prevention of allograft rejection by in vitro generated tolerogenic dendritic cells. Transplant immunology, 2003. 11(3-4): p. 295-306.
23. Popov, I., et al., Preventing autoimmune arthritis using antigen-specific immature dendritic cells: a novel tolerogenic vaccine. Arthritis research & therapy, 2006. 8(5): p. R141.
24. Luketic, L., et al., Antigen presentation by exosomes released from peptide-pulsed dendritic cells is not suppressed by the presence of active CTL. Journal of immunology, 2007. 179(8): p. 5024-32.
25. Segura, E., S. Amigorena, and C. Thery, Mature dendritic cells secrete exosomes with strong ability to induce antigen-specific effector immune responses. Blood cells, molecules & diseases, 2005. 35(2): p. 89-93.
26. Ruffner, M. A., et al., B7-1/2, but not PD-L1/2 molecules, are required on IL-10-treated tolerogenic DC and DC-derived exosomes for in vivo function. European journal of immunology, 2009. 39(11): p. 3084-90.
27. Yang, X., et al., Exosomes derived from immature bone marrow dendritic cells induce tolerogenicity of intestinal transplantation in rats. The Journal of surgical research, 2011. 171(2): p. 826-32.
28. Peche, H., et al., Induction of tolerance by exosomes and short-term immunosuppression in a fully MHC-mismatched rat cardiac allograft model. American journal of transplantation: official journal of the American Society of Transplantation and the American Society of Transplant Surgeons, 2006. 6(7): p. 1541-50.
29. Kim, S. H., et al., MHC class II+ exosomes in plasma suppress inflammation in an antigen-specific and Fas ligand/Fas-dependent manner. Journal of immunology, 2007. 179(4): p. 2235-41.
30. Marleau, A. M., et al., Chimerism of murine fetal bone marrow by maternal cells occurs in late gestation and persists into adulthood. Laboratory investigation; a journal of technical methods and pathology, 2003. 83(5): p. 673-81.
31. Kara, R. J., et al., Fetal Cells Traffic to Injured Maternal Myocardium and Undergo Cardiac Differentiation. Circulation research, 2011.
32. Khashan, A. S., et al., Pregnancy and the risk of autoimmune disease. PloS one, 2011. 6(5): p. e19658.
33. Ernerudh, J., G. Berg, and J. Mjosberg, Regulatory T helper cells in pregnancy and their roles in systemic versus local immune tolerance. American journal of reproductive immunology, 2011.66 Suppl 1: p. 31-43.
34. Lin, Q. D. and L. H. Qiu, Pathogenesis, diagnosis, and treatment of recurrent spontaneous abortion with immune type. Frontiers of medicine in China, 2010. 4(3): p. 275-9.
35. Pandey, M. K., R. Rani, and S. Agrawal, An update in recurrent spontaneous abortion. Archives of gynecology and obstetrics, 2005. 272(2): p. 95-108.
36. Frangsmyr, L., et al., Cytoplasmic microvesicular form of Fas ligand in human early placenta: switching the tissue immune privilege hypothesis from cellular to vesicular level. Molecular human reproduction, 2005. 11(1): p. 35-41.
37. Taylor, D. D., S. Akyol, and C. Gercel-Taylor, Pregnancy-associated exosomes and their modulation of T cell signaling. Journal of immunology, 2006. 176(3): p. 1534-42.
38. Sabapatha, A., C. Gercel-Taylor, and D. D. Taylor, Specific isolation of placenta-derived exosomes from the circulation of pregnant women and their immunoregulatory consequences. American journal of reproductive immunology, 2006. 56(5-6): p. 345-55.
39. Hedlund, M., et al., Human placenta expresses and secretes NKG2D ligands via exosomes that down-modulate the cognate receptor expression: evidence for immunosuppressive function. Journal of immunology, 2009. 183(1): p. 340-51.
40. Forger, F., et al., Pregnancy induces numerical and functional changes of CD4+CD25 high regulatory T cells in patients with rheumatoid arthritis. Annals of the rheumatic diseases, 2008. 67(7): p. 984-90.
41. Airas, L., et al., Immunoregulatory factors in multiple sclerosis patients during and after pregnancy: relevance of natural killer cells. Clinical and experimental immunology, 2008. 151(2): p. 235-43.
42. Gatson, N. N., et al., Induction of pregnancy during established EAE halts progression of CNS autoimmune injury via pregnancy-specific serum factors. Journal of neuroimmunology, 2011. 230(1-2): p. 105-13.
43. Taylor, D. D. and C. Gercel-Taylor, Tumour-derived exosomes and their role in cancer-associated T-cell signalling defects. British journal of cancer, 2005. 92(2): p. 305-11.
44. Valenti, R., et al., Tumor-released microvesicles as vehicles of immunosuppression. Cancer research, 2007. 67(7): p. 2912-5.
45. Greten, T. F., M. P. Manns, and F. Korangy, Myeloid derived suppressor cells in human diseases. International immunopharmacology, 2011. 11(7): p. 802-7.

46. Szajnik, M., et al., Tumor-derived microvesicles induce, expand and up-regulate biological activities of human regulatory T cells (Treg). PloS one, 2010. 5(7): p. e11469.
47. Weiner, H. L., et al., Oral tolerance. Immunological reviews, 2011. 241(1): p. 241-59.
48. Wei, W., et al., A multicenter, double-blind, randomized, controlled phase III clinical trial of chicken type II collagen in rheumatoid arthritis. Arthritis research & therapy, 2009. 11(6): p. R180.
49. Benson, J. M., et al., Oral administration of myelin basic protein is superior to myelin in suppressing established relapsing experimental autoimmune encephalomyelitis. Journal of immunology, 1999. 162(10): p. 6247-54.
50. Hafler, D. A., et al., Oral administration of myelin induces antigen-specific TGF-beta 1 secreting T cells in patients with multiple sclerosis. Annals of the New York Academy of Sciences, 1997. 835: p. 120-31.
51. Ostman, S., M. Taube, and E. Telemo, Tolerosome-induced oral tolerance is MHC dependent. Immunology, 2005. 116(4): p. 464-76.
52. Almqvist, N., et al., Serum-derived exosomes from antigen-fed mice prevent allergic sensitization in a model of allergic asthma. Immunology, 2008. 125(1): p. 21-7.
53. Meng, X., et al., Endometrial regenerative cells: a novel stem cell population. Journal of translational medicine, 2007. 5: p. 57.
54. Ichim, T. E., et al., Placental mesenchymal and cord blood stem cell therapy for dilated cardiomyopathy. Reproductive biomedicine online, 2008. 16(6): p. 898-905.
55. Ichim, T. E., et al., Feasibility of combination allogeneic stem cell therapy for spinal cord injury: a case report. International archives of medicine, 2010. 3: p. 30.
56. Yang, W. Z., et al., Human umbilical cord blood-derived mononuclear cell transplantation: case series of 30 subjects with hereditary ataxia. Journal of translational medicine, 2011.9: p. 65.
57. Kebriaei, P. and S. Robinson, Treatment of graft-versus-host-disease with mesenchymal stromal cells. Cytotherapy, 2011. 13(3): p. 262-8.
58. Sun, L., et al., Mesenchymal stem cell transplantation reverses multiorgan dysfunction in systemic lupus erythematosus mice and humans. Stem cells, 2009. 27(6): p. 1421-32.
59. Uccelli, A. and D. J. Prockop, Why should mesenchymal stem cells (MSCs) cure autoimmune diseases? Current opinion in immunology, 2010. 22(6): p. 768-74.
60. Ra, J. C., et al., Stem cell treatment for patients with autoimmune disease by systemic infusion of culture-expanded autologous adipose tissue derived mesenchymal stem cells. Journal of translational medicine, 2011.9: p. 181.
61. Lai, R. C., T. S. Chen, and S. K. Lim, Mesenchymal stem cell exosome: a novel stem cell-based therapy for cardiovascular disease. Regenerative medicine, 2011. 6(4): p. 481-92.
62. Alvarez-Erviti, L., et al., Delivery of siRNA to the mouse brain by systemic injection of targeted exosomes. Nature biotechnology, 2011. 29(4): p. 341-5.

What is claimed is:

1. A method of treating a patient comprising the steps of:
   a) extracting endometrial regenerative cells (ERCs);
   b) culturing said ERCs for a sufficient time period, under conditions permissible for exosome production;
   c) collecting exosomes produced by said ERCs;
   d) concentrating said collected exosomes; and
   e) administering said concentrated exosomes and said ERCs to said patient,
   wherein said patient has an autoimmune condition selected from the group consisting of: diabetes; multiple sclerosis; rheumatoid arthritis; Hashimoto's thyroiditis; graft rejection; graft versus host disease; and systemic lupus erythromatosis.

2. The method of claim 1, wherein said ERCs are induced to increase exosome production.

3. The method of claim 2, wherein said induction of exosome production from said ERCs is achieved by treatment of said ERCs with cytokines.

4. The method of claim 1, wherein said exosomes are concentrated by ultracentrifugation; column chromatography; size exclusion; or filtration through a device containing an affinity matrix selective towards exosomes.

5. The method of claim 1, wherein said exosomes are transfected with a genetic material, and wherein said genetic material is delivered into an immune cell.

6. The method of claim 1, wherein said exosomes are produced from ERCs transferred with a genetic material, and wherein said genetic material is delivered into an immune cell.

7. A method of treating a patient comprising the steps of:
   a) extracting endometrial regenerative cells (ERCs);
   b) culturing said ERCs for a sufficient time period, under conditions permissible for exosome production;
   c) collecting exosomes generated by said ERC population;
   d) concentrating said collected exosomes to at least 1 µg/mL; and
   e) administering 1-2 µg of said concentrated exosomes and at least 100,000 of said ERCs to said patient,
   wherein said patient has an autoimmune condition selected from the group consisting of: diabetes; multiple sclerosis; rheumatoid arthritis; Hashimoto's thyroiditis; graft rejection; graft versus host disease; and systemic lupus erythromatosis.

8. The method of claim 7, further comprising incorporating one or more autoantigens into said concentrated exosomes.

9. The method of claim 7, further comprising transfecting said ERCs with one or more autoantigen genes, wherein the one or more autoantigens are representative of said autoimmune condition.

10. A method of treating a patient having an autoimmune condition comprising the steps of:
    a) obtaining endometrial regenerative cells (ERCs);
    b) introducing into said ERCs an antigen, wherein said antigen is present in one or more exosomes produced by said ERCs;
    c) purifying and concentrating said exosomes to at least 1 µg/mL;
    d) administering an amount of said concentrated exosomes and an amount of said ERCs into the patient to suppress a biological pathway associated with an immune pathway associated with the autoimmune condition,
    wherein said autoimmune condition is selected from the group consisting of: diabetes; multiple sclerosis; rheumatoid arthritis; Hashimoto's thyroiditis; graft rejection; graft versus host disease; and systemic lupus erythromatosis.

11. The method of claim 10, wherein said ERCs are cultured in a DMEM F12 medium comprising approximately 10% fetal calf serum for a period of 1-100 hours to produce said exosomes.

12. The method of claim 10, wherein said exosomes are concentrated by ultracentrifugation; column chromatography; size exclusion; or filtration through a device containing an affinity matrix selective towards exosomes.

13. The method of claim 10, wherein said antigen is incorporated into said exosome-producing ERCs by transfection with a gene encoding said antigen; transfection with an antigenic protein; or transfection with an antigenic peptide.

14. The method of claim 10, wherein said antigen is loaded into said exosomes.

15. The method of claim 14, wherein said loading is by a chemical means.

* * * * *